US012262995B2

(12) United States Patent
Kim

(10) Patent No.: US 12,262,995 B2
(45) Date of Patent: Apr. 1, 2025

(54) ART PSYCHOLOGICAL ANALYSIS APPARATUS USING VOICE, TEXT, AND PICTURE DATA AND ART PSYCHOLOGICAL ANALYSIS METHOD USING THE SAME

(71) Applicant: I-SCREAM ARTS CO., LTD., Seoul (KR)

(72) Inventor: Ji-hoon Kim, Seoul (KR)

(73) Assignee: I-SCREAM ARTS CO., LTD., Seoul (KR)

( * ) Notice: Subject to any disclaimer, the term of this patent is extended or adjusted under 35 U.S.C. 154(b) by 8 days.

(21) Appl. No.: 18/350,826

(22) Filed: Jul. 12, 2023

(65) Prior Publication Data

US 2023/0346280 A1 Nov. 2, 2023

Related U.S. Application Data

(63) Continuation of application No. PCT/KR2021/016753, filed on Nov. 16, 2021.

(30) Foreign Application Priority Data

Sep. 3, 2021 (KR) .................. 10-2021-0117708
Nov. 11, 2021 (KR) .................. 10-2021-0154398

(51) Int. Cl.
*G09B 19/00* (2006.01)
*A61B 5/00* (2006.01)
(Continued)

(52) U.S. Cl.
CPC ............ *A61B 5/165* (2013.01); *A61B 5/4803* (2013.01); *A61B 5/7267* (2013.01); *G09B 19/00* (2013.01);
(Continued)

(58) Field of Classification Search
CPC ..... A61B 5/165; A61B 5/4803; A61B 5/7267; G09B 19/00
See application file for complete search history.

(56) References Cited

FOREIGN PATENT DOCUMENTS

| KR | 10-1524753 B1 | 6/2015 |
|----|---------------|--------|
| KR | 10-1898385 B1 | 9/2018 |

(Continued)

*Primary Examiner* — Kesha Frisby
(74) *Attorney, Agent, or Firm* — NKL Law; Jae Youn Kim

(57) ABSTRACT

Provided is an art psychological analysis apparatus using voice, text, and picture data which analyzes an emotion of a test taker using voice data, text data, and picture data extracted from a voice of the test taker at the time of the art psychological test and analyzes a test taker's personality using a meaningful picture subject to understand the psychology and an art psychological analysis method using the same. The art psychological analysis apparatus using voice, a text, and picture data may include a user interface for providing an interaction environment to a user who is a test taker, a data extraction unit which extracts voice data from a voice of the user input through the user interface during an art psychological test and extracts text data from the voice data, an emotion analysis unit which analyzes an emotion of the user from picture data input by the user through the user interface using the voice data and text data extracted from the data extraction unit, a personality analysis unit which analyzes a personality of the user according to a picture subject of the picture data input by the user together with the picture data, through the user interface, a psychological state analysis unit which analyzes a psychological state of the user based on the emotion of the user analyzed by the emotion analysis unit and the personality of the user analyzed by the personality analysis unit, and a database which stores information about the user's psychological state analyzed by the psychological state analysis unit.

9 Claims, 5 Drawing Sheets

(51) Int. Cl.
*A61B 5/16* (2006.01)
*G10L 15/06* (2013.01)
*G10L 15/22* (2006.01)
*G10L 15/26* (2006.01)
*G10L 25/63* (2013.01)

(52) U.S. Cl.
CPC ............ *G10L 15/063* (2013.01); *G10L 15/22* (2013.01); *G10L 15/26* (2013.01); *G10L 25/63* (2013.01)

(56) References Cited

FOREIGN PATENT DOCUMENTS

| KR | 10-1926836 B1 | 12/2018 |
|---|---|---|
| KR | 10-1942444 B1 | 1/2019 |
| KR | 10-2021-0027769 A | 3/2021 |

… ture data which analyzes an emotion of a test taker using voice data and text data extracted from a voice of the test taker at the time of the art psychological test, and picture data to analyze a test taker's personality using a meaningful picture subject to understand the psychology, and an art psychological analysis method using the same.

Specifically, an object of the present disclosure is to provide an art psychological analysis apparatus using voice, text, and picture data in which an artificial intelligence model generated using voice data and text data is trained by self-distillation or self-supervised learning technique to analyze an emotion of a test taker from picture data which is drawn by the test taker, and an art psychological analysis method using the same.

Further, an object of the present disclosure is to provide an art psychological analysis apparatus using voice, text, and picture data which determines whether a distribution status of clusters classified according to picture subjects by means of an image clustering is similar to a distribution predicted by the artificial intelligence model, and verifies a validity of an artificial intelligence model, and an art psychological analysis method using the same.

Technical objects to be achieved in the present disclosure are not limited to the aforementioned technical objects, and another not-mentioned technical object will be clearly understood by those skilled in the art from the description below.

Technical Solution

In order to achieve the above-described objects, an art psychological analysis apparatus using voice, text, and picture data of the present disclosure may include: a user interface for providing an interaction environment to a user who is a test taker; a data extraction unit which extracts voice data from a voice of the user input through the user interface during an art psychological test, and extracts text data from the voice data; an emotion analysis unit which analyzes an emotion of the user from picture data input by the user through the user interface using the voice data and text data extracted from the data extraction unit; a personality analysis unit which analyzes a personality of the user according to a picture subject of the picture data input by the user together with the picture data, through the user interface; a psychological state analysis unit which analyzes a psychological state of the user based on the emotion of the user analyzed by the emotion analysis unit and the personality of the user analyzed by the personality analysis unit; and a database which stores information about the user's psychological state analyzed by the psychological state analysis unit.

Further, the emotion analysis unit may include an artificial intelligence model unit which performs the training using an emotion analysis model in which the training data is constructed by labeling the emotion analysis result according to the voice data and text data extracted from a voice input together with picture data through the user interface to analyze the emotion of the user.

Further, the artificial intelligence model unit may include: a first artificial intelligence model which distillates by itself based on a self-distillation technique and analyzes the emotion with picture data by smoothing the emotion analysis result of the emotion analysis model with a soft label and then by setting to a ground truth.

Further, the artificial intelligence model unit may include: a second artificial intelligence model which is trained in advance by a pretext task set by a second user who is a tester

ART PSYCHOLOGICAL ANALYSIS APPARATUS USING VOICE, TEXT, AND PICTURE DATA AND ART PSYCHOLOGICAL ANALYSIS METHOD USING THE SAME

TECHNICAL FIELD

The present disclosure relates to an art psychological analysis apparatus using voice, text, and picture data and an art psychological analysis method using the same, and more particularly, to a technique which analyzes an emotion of a test taker using voice data and text data extracted from a voice of the test taker at the time of the art psychological test, and picture data to analyze a test taker's personality using a meaningful picture subject to understand the psychology.

BACKGROUND ART

A lot of technologies are being developed to analyze a psychological state or personality of a test taker using a text or voice. However, a method of examining the test taker's psychology by collecting text, voice, and picture data is not generally used, and specifically, the psychological test using only picture data is not highly reliable without additional information such as an order of drawing objects.

That is, it is very difficult to figure out a psychological state or personality of a test taker only using picture data, and there are not many proved psychological test methods. The subjectivity and questions and answers of the tester are required to properly figure out the psychological state or the personality of the test taker. Even though there is various picture data, the psychological state is not always consistent, but may vary depending on the situation.

Accordingly, when an artificial intelligence model for an art psychological test is constructed, an emotion and a psychological state of the test taker need to be accurately figured out at the time of psychological test.

In the meantime, as a representative example of the art psychological test which analyzes a psychological state of a test taker using picture data, there is an HTP test. According to the HTP test, it is requested to draw a house, a tree, and a person, and then a psychological state of the test taker who draws the picture is analyzed from art information of a shape, a color, and a positon of the picture so that test takers of all age groups may easily take the test. Accordingly, the HTP test is widely recognized for its usefulness.

However, it is not easy to prove the validity of the evaluation method for a new picture so that subjects (objects) of the picture data used for the art psychological test such as HTP test are not diverse. Further, in order to derive a standardized and general psychological analysis result, test takers having a specific personality need to draw pictures with a similar pattern. However, in this case, it is not easy to consider that the pattern is generated only from the intended part of the subject so that even though the picture subject is determined based on the psychology, an expected psychological analysis result may not be derived. Further, there are many subjective factors, so that even though an expected result is obtained with a common evaluation for several test takers, it is difficult to determine whether the same result is possible for a new test taker.

DISCLOSURE

Technical Problem

An object of the present disclosure is to provide an art psychological analysis apparatus using voice, text, and picbased on a self-supervised learning technique and analyzes an emotion with picture data by setting the emotion analysis result of the emotion analysis model to the ground truth as a pseudo label.

Further, the emotion analysis unit may include: a first emotion analysis unit which is trained with the first artificial intelligence model to analyze an emotion of the user with picture data input through the user interface; and a second emotion analysis unit which is trained with the second artificial intelligence model to analyze an emotion of the user with picture data input through the user interface and maintains an operation standby state during the operation of the first emotion analysis unit and operates in an operation standby state of the first emotion analysis unit.

Further, when the user omits the inputting of a picture subject of the picture data through the user interface, the first emotion analysis unit may be converted to an operation standby state.

Further, the emotion analysis unit may include: a third artificial intelligence model trained to determine whether a picture subject of the picture data is valid by determining whether a distribution status of a cluster is similar to a predicted distribution status of a cluster by image clustering which divides similar picture data according to a picture subject by clusters and to classify the cluster by personalities to analyze the personality by the picture subject.

Further, the art psychological analysis apparatus using voice, text, and picture data of the present disclosure may further include: a communication unit which communicates with a terminal of the second user.

Further, the terminal of the second user may include: a second user interface which provides, to the second user, information about a psychological state of the user analyzed by the psychological state analysis unit which is to be stored in the database, and allows the second user to input a psychological analysis opinion about an emotion and a personality of the user analyzed by the second user from information about a psychological state of the user.

Further, the database may store an art psychological analysis opinion about the emotion and the personality of the user which is analyzed by the second user and provided through the second user interface and the communication unit.

When the information about the psychological state of the user is stored in the database, the user interface outputs information about the psychological state of the user and when an art psychological analysis opinion about the emotion and the personality of the user is stored in the database, the user interface may output the information about the psychological state of the user along with the art psychological analysis opinion about the emotion and the personality of the user.

An art psychological analysis method using an art psychological analysis apparatus using voice, text, and picture data of the present disclosure may include: training a data extraction unit, an emotion analysis unit, a personality analysis unit, and a psychological state analysis unit; inputting, by a user, picture data, voice, and a picture subject of the picture data to a user interface during an art psychological test; extracting voice data from a voice of the user, and extracting text data from the voice data, by the data extraction unit; analyzing an emotion of the user from the picture data using voice data and text data of the user, by the emotion analysis unit; analyzing a personality of the user according to a picture subject of the picture data, by the personality analysis unit; analyzing, by the psychological state analysis unit, a psychological state of the user based on an emotion of the user analyzed by the emotion analysis unit and a personality of the user analyzed by the personality analysis unit; and storing information about a psychological state of the user analyzed by the psychological state analysis unit in a database.

Further, the art psychological analysis method using an art psychological analysis apparatus using voice, text, and picture data of the present disclosure may include: outputting information about a psychological state of the user through the user interface; inputting an art psychological analysis opinion about an emotion and a personality analyzed from information about a psychological state of the user by the second user interface to be stored in the database after receiving information about a psychological state of the user by the second user through a second user interface and a communication unit provided in a terminal of the second user who is a tester; and outputting information about a psychological state of the user and an art psychological analysis opinion about an emotion and a personality of the user together through the user interface.

A computer program stored in a computer readable recording medium to execute the art psychological analysis method using an art psychological analysis apparatus using voice, text, and picture data of the present disclosure may be provided.

Advantageous Effects

According to the present disclosure, a high performance of artificial intelligence model which analyzes the emotion of a test taker with voice data, text data, and picture data is generated, and various emotions of the test taker may be analyzed from one picture data.

Further, according to the present disclosure, as compared with a generalized art psychological test such as HTP test of the related art, various picture subjects can be selected, thereby improving the validity and the versatility of the art psychological analysis test.

A technical object to be achieved in the present disclosure is not limited to the aforementioned effects, and another not-mentioned effects will be obviously understood by those skilled in the art from the description below.

BEST MODE

Figure 1:
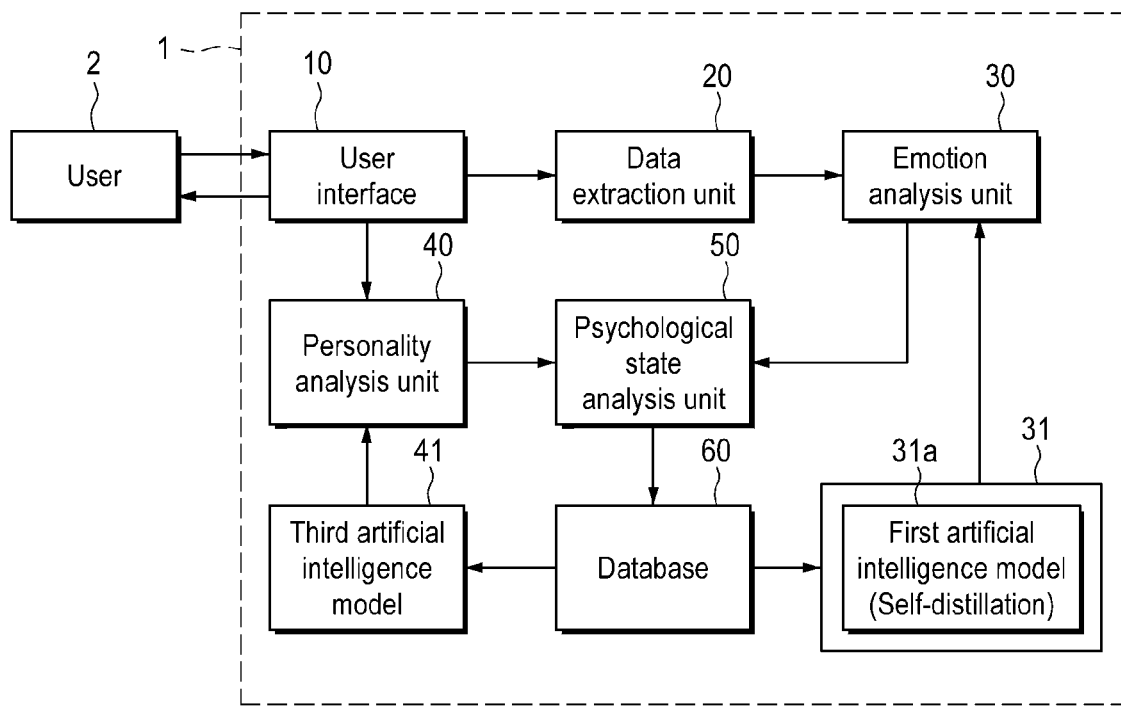
FIG. 1 is a block diagram schematically illustrating an art psychological analysis apparatus using voice, text, and picture data according to an exemplary embodiment of the present disclosure.

Hereinafter, exemplary embodiments of the present disclosure will be described more fully with reference to the accompanying drawings for those skilled in the art to easily implement the present disclosure. Description of the present disclosure is just an embodiment for structural and functional description so that the scope of the present disclosure is not interpreted to be limited by the embodiment described in the specification. That is, the embodiment may be modified in various forms so that it is understood that the scope of the present disclosure has equivalents which are capable of implementing the technical spirit. Further, it does not mean that the specific embodiment includes the object or effect proposed in the present disclosure or include only the effect so that it is not understood that the scope of the present disclosure is limited thereby.

In the meantime, meanings of terms described in the present disclosure can be understood as follows.

The terms "first" or "second" are used to distinguish one component from the other component so that the scope should not be limited by these terms. For example, a first component may be referred to as a second component, and similarly, a second component may be referred to as a first component. It should be understood that, when it is described that an element is "connected" to another element, the element may be directly connected to the other element or connected to the other element through a third element. In contrast, it should be understood that, when it is described that an element is directly connected to another element, no element is present between the element and the other element. Other expressions which describe the relationship between components, that is, "between" and "directly between", or "adjacent to" and "directly adjacent to" need to be interpreted by the same manner.

Unless the context apparently indicates otherwise, it should be understood that terms "include" or "have" indicate that a feature, a number, a step, an operation, a component, a part or the combination thereof described in the specification is present, but do not exclude a possibility of presence or addition of one or more other features, numbers, steps, operations, components, parts or combinations thereof, in advance.

Unless they are contrarily defined, all terms used herein including technological or scientific terms have the same meaning as those generally understood by a person with ordinary skill in the art. Terms which are defined in a generally used dictionary should be interpreted to have the same meaning as the meaning in the context of the related art but are not interpreted as an ideally or excessively formal meaning if it is not clearly defined in the present disclosure.

An art psychological analysis apparatus 1 using voice, text, and picture data of the present disclosure (hereinafter, referred to as an art psychological analysis apparatus 1) is a system which analyzes an emotion of a test taker using voice data, and text data, extracted from a voice of the test taker at the time of the art psychological test, and picture data. The art psychological analysis apparatus 1 analyzes a test taker's personality using a meaningful picture subject to understand the psychology, and components of the system to implement the present disclosure are as follows.

FIG. 1 is a block diagram schematically illustrating an art psychological analysis apparatus using voice, text, and picture data according to an exemplary embodiment of the present disclosure.

Referring to FIG. 1, an art psychological analysis apparatus 1 according to an exemplary embodiment of the present disclosure includes a user interface 10, a data extraction unit 20, an emotion analysis unit 30, a personality analysis unit 40, a psychological state analysis unit 50, and a database 60.

The user interface 10 provides an environment in which a user 2 who is a test taker to receive the art psychological service interacts with the art psychological analysis apparatus 1, and is a concept including a hardware device and a software program to receive an instruction from the user 2 and convert the instruction into electronic data. For example, an input device such as a keyboard, a mouse, and a touch pen, an output device such as a display, and a drawing application which processes data, such as contours and colors, input through the input device to display the data on the output device in real time may be included.

Further, picture data which is drawn by the user 2 during the art psychological test is input to the user interface 10, and the picture data of the present disclosure may be a picture including an object serving as an evaluation element of the art psychological analysis and an item which forms the object.

In the present disclosure, the art psychological test may be an HTP test which asks to draw at least one of a house, a tree, and a people which is an object and then analyzes a psychological state of the user from information such as a shape, a color, and a position of the picture. However, the method for analyzing the personality of the user 2 with a picture subject of various picture data is not limited. If the object is a house, as an item constituting the object, house frames (a roof, a wall, and a chimney), windows, and doors may be included and if the object is a tree, stems, roots, leaves, and fruits may be included.

When the picture data is input, the user interface 10 requests the user 2 to explain the picture data to input the voice of the user 2 including explanation of the picture data. After requesting the voice recording through the user interface 10, the user 2 inputs the explanation of the picture data by a voice, or after outputting a question message on the display of the art psychological analysis apparatus 1, inputs the explanation of the picture data by a voice.

The user interface 10 requests the user 2 to input the picture subject in order to input the picture subject of the picture data before inputting the picture data or after inputting the picture data, as well as the voice of the user 2 and the picture data. The user 2 may select the classified picture subject or input the picture subject in the form of a text, by means of the user interface 10.

The picture subject which is capable of being input by the user interface 10 is not limited to the house, the tree, and the people as in the HTP test, but may be set to various subjects, such as animals, insects, buildings, and transportations.

The data extraction unit 20 extracts voice data from the voice of the user 2 input through the user interface 10 during the art psychological test, and extracts text data from the voice data.

In the present disclosure, the data extraction unit 20 extracts the voice data by separating a waveform of a sound source in which a voice of the user 2 and a noise excluding the voice are mixed into a voice waveform and a noise waveform, and may extract text data from the voice data using a voice-text conversion program.

The emotion analysis unit 30 analyzes the emotion of the user 2 from the picture data input by the user 2 through the user interface 10 using voice data and text data extracted from the data extraction unit 20.

At this time, the emotion is generally a feeling that the user 2 may feel about certain phenomenon or things, such as 'joy', 'anger', 'sadness', 'pleasure', 'love', 'hate', 'desire', 'impression', 'confidence', 'jealousy', 'happiness', 'hope', 'despair', 'fear', 'excitement', 'disappointment', 'longing', 'worry', and 'expectation'.

In the present disclosure, the emotion analysis unit 30 is trained by the artificial intelligence model unit 31 to analyze the emotion of the user 2. The artificial intelligence model unit 31 performs the training using an emotion analysis model in which training data is constructed by labeling an emotion analysis result according to voice data and text data extracted from the voice which is input along with the picture data through the user interface 10.

Further, the artificial intelligence model unit 31 includes a first artificial intelligence model 31a for analyzing an emotion of the user 2. The first artificial intelligence model 31a distills by itself based on the self-distillation, and smooths the emotion analysis result of the emotion analysis model to a soft label, and then sets to a ground truth to analyze the emotion with the picture data.

At this time, the self-distillation is one of knowledge distillation methods, and the knowledge distillation is a method of training a small model (student network) to be actually used from a previously trained large model (teacher network). However, the self-distillation has a problem in that the size is significantly increased in proportion to a performance of the model. In order to solve the problem of the knowledge distillation model, the self-distillation learns the distillation by itself by utilizing components in the model without relying on a separate model, and has an advantage in terms of light weight. That is, the emotion analysis model may be an internal component of the first artificial intelligence model 31.

The first artificial intelligence model 31a smooths an emotion analysis result which is a hard label to a soft label to prevent the emotion analysis unit 30 from analyzing only one emotion from one picture data. People does not feel emotion biased toward one side of a certain phenomenon or thing, but may feel various emotions. However, when the emotion analysis unit 30 analyzes an emotion of the picture data by setting the hard label as an actual value, only one emotion may be analyzed for each picture data. In contrast, when the emotion analysis result is smoothed to a soft label by the first artificial intelligence model 31a, the emotion analysis unit 30 configures the emotion of the user 2 with a value of 0 to 1.0 from the picture data to analyze various emotions. As a specific example, the emotion of the user 2 may be analyzed from the picture data such that anxiety is 0.3 and horror is 0.7.

In the meantime, the artificial intelligence model unit 31 is not limited to include the first artificial intelligence model 31a, and a second artificial intelligence model 31a which is trained based on the other learning technique may be included instead of the first artificial intelligence model 31a.

Figure 2:
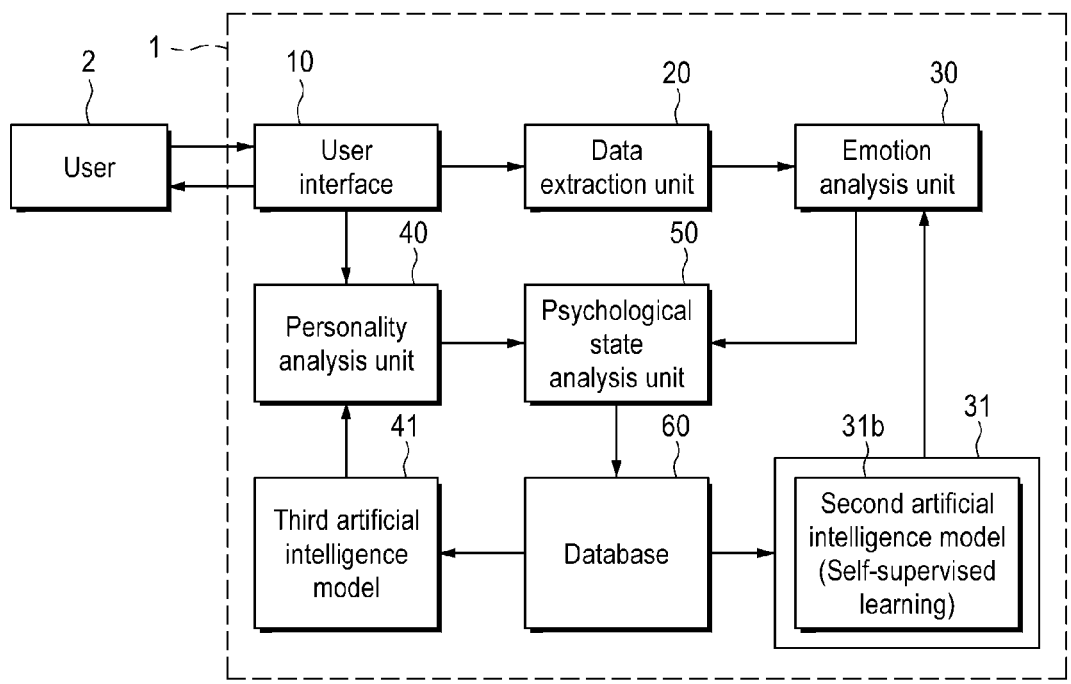
FIG. 2 is a block diagram schematically illustrating an art psychological analysis apparatus using voice, text, and picture data according to an exemplary embodiment of the present disclosure, in which an artificial intelligence model unit of FIG. 1 is modified.

FIG. 2 is a block diagram schematically illustrating an art psychological analysis apparatus using voice, text, and picture data according to an exemplary embodiment of the present disclosure, in which an artificial intelligence model unit of FIG. 1 is modified.

Referring to FIG. 2, the artificial intelligence model unit 31 may include a second artificial intelligence model 31b instead of the first artificial intelligence model 31a which analyzes the emotion of the user 2. The second artificial intelligence model 31b is previously trained through a pretext task set by a second user 3 who is a tester based on the self-supervised learning technique, and sets the emotion analysis result of the emotion analysis model to an actual value as a pseudo label to analyze the emotion with the picture data.

At this time, the pseudo label refers that a probability which is predicted as the highest probability is set by an actual value.

Further, the task set by the second user 3 refers to a problem that analyzes the emotion of the test taker to a soft label using voice data, text data, and picture data so that the second artificial intelligence model 31b analyzes the emotion with the first artificial intelligence model 31a and values of 0 to 1.0.

The second artificial intelligence model 31b uses a psychological analysis result of the emotion analysis model as a pseudo label to save a time and cost for constructing the model by omitting a labeling process of the emotion analysis result according to the voice data and the text data.

The personality analysis unit 40 is trained by a third artificial intelligence model 41 to analyze a personality of the user 2 according to a picture subject of picture data input by the user 2 together with the picture data through the user interface 10. The personality includes a personality type which may be derived through a personality type test (for example, MBTI), such as "introvert" and "extrovert".

Even though a training method to analyze the personality with a picture subject of the picture data is not limited, according to the present disclosure, the third artificial intelligence model 41 is trained to measure similarities for every picture subject of each picture data by image clustering, and then classified the similar picture data for every picture subject into clusters. And the third artificial intelligence model 41 classifies the clusters by personalities as represented in Table 1 to analyze the personality based on the picture subject.

TABLE 1

|  | Personality 1 | Personality 2 | Personality 3 | Personality 4 | Personality 5 |
|---|---|---|---|---|---|
| Picture subject 1 | O | — | — | — | O |
| Picture subject 2 | — | O | O | — | — |
| Picture subject 3 | — | — | — | O | — |

At this time, the similarity for every picture subject is measured based on a pixel value unit by a K-means technique or based on a Euclid distance within a specific arbitrary point. Alternatively, the similarity for every picture subject may be measured by a deep learning technique such as Siamese-Network which measures the similarity based on how much two images match by image modification. In the meantime, the third artificial intelligence model 41 needs to be determined whether the cluster classified by the picture subjects is appropriately classified for every personality during the training process, and the determination may be performed by the clustering distribution chart.

Figure 3A:
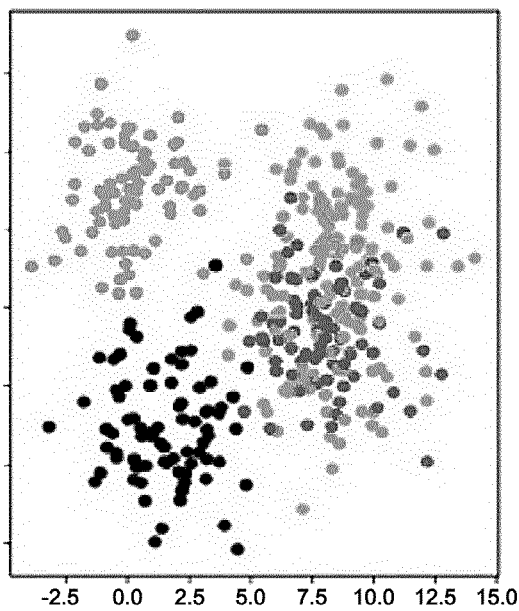
FIGS. 3(a)-3(b) are diagrams illustrating clustering distribution according to every picture subject for explaining a validity verification process of a personality analysis unit according to an exemplary embodiment of the present disclosure.
Figure 3B:
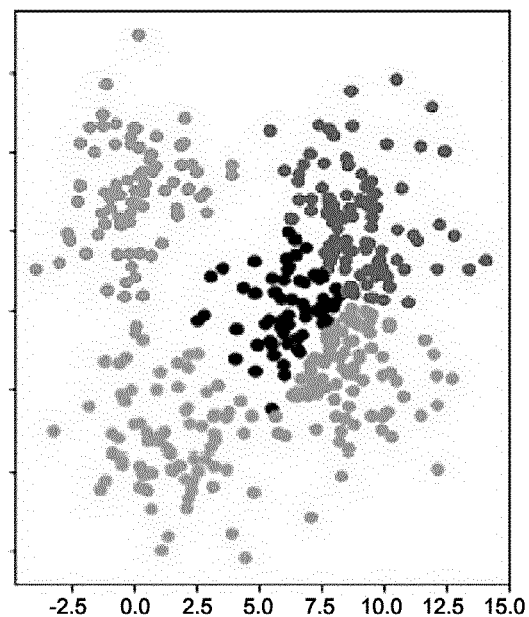

FIGS. 3(a)-3(b) are diagrams illustrating clustering distribution for every picture subject for explaining a validity verification process of a personality analysis unit according to an exemplary embodiment of the present disclosure.

Referring to FIG. 3(a), some clusters among a plurality of clusters classified by picture subjects may be distributed in a mixed form, which means that the clusters classified by the picture subjects are not appropriately classified by the personalities.

At this time, when a distribution status of the cluster predicted by the third artificial intelligence model 41 is not similar to the cluster distribution status illustrated in FIG. 3(a), the picture data is not drawn in accordance with the picture subject so that it may be determined that an actual meaningful art psychological test is not performed.

Referring to FIG. 3(b), the plurality of clusters classified by picture subjects may be separately distributed, which means that the clusters classified by the picture subjects are appropriately classified by the personalities.

At this time, when a distribution status of the cluster predicted by the third artificial intelligence model 41 is similar to the cluster distribution status illustrated in FIG. 3(a), the picture data is drawn in accordance with the picture subject so that it may be determined that an actual meaningful art psychological test is performed. The validity of the third artificial intelligence model 41 may be proved by the image clustering.

Moreover, the third artificial intelligence model 41 is desirably trained until the plurality of clusters which is classified by picture subjects is appropriately classified according to the personality to induce the personality analysis unit 40 to accurately analyze the personalities with the picture subject.

Referring to FIG. 1 again, the psychological state analysis unit 50 is trained with the artificial intelligence model to analyze the psychological state of the user 2 based on the emotion of the user 2 analyzed by the emotion analysis unit 30 and the personality of the user 2 analyzed by the personality analysis unit 40.

At this time, an artificial intelligence model of the psychological state analysis unit 50 refers to a learning model which is configured by a plurality of layers to implement a function similar to a human neural network, and an artificial neural network model such as recurrent neural network (RNN), convolutional neural network (CNN), and an attention based model may be used. The artificial intelligence model of the psychological state analysis unit 50 may be trained to analyze a psychological state of the user 2 by searching from art based psychological analysis information which is stored in advance in the database 60.

Further, the art based psychological analysis information includes psychological analysis result data about which object and item are included or omitted by the user 2 to draw the picture, whether an object and the item are drawn large or small, which difference is present between the object and item and the shape in a general socially accepted idea, accumulated face-to-face or non-contact psychological counseling data, and research paper related to the art based psychological analysis, and may be updated by an independent psychological analysis result obtained from the art psychological analysis apparatus 1.

When the psychological state analysis unit 50 analyzes a psychological state of the user 2, the database 60 stores information about a psychological state of the user 2.

At this time, when the psychological state information of the user 2 is stored in the database 60, the user interface 10 outputs information about the psychological state of the user 2 stored in the database 60 on a display of the art psychological analysis apparatus 1, and may provide an art psychological analysis result to the user 2 thereby.

Hereinafter, an art psychological analysis apparatus 1 according to another exemplary embodiment of the present disclosure will be described in more detail with respect to the difference from the art psychological analysis apparatus 1 according to the exemplary embodiment of the present disclosure.

Figure 4:
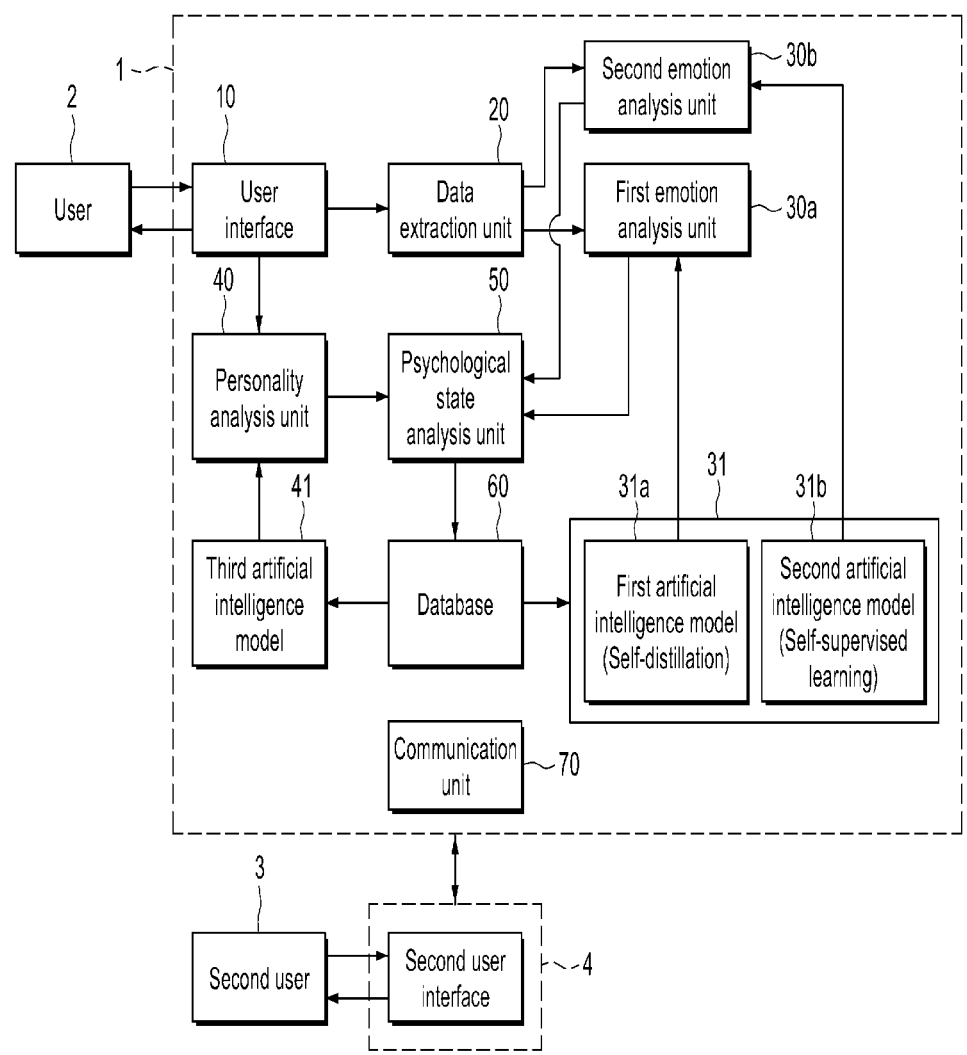
FIG. 4 is a block diagram schematically illustrating an art psychological analysis apparatus using voice, text, and picture data according to another exemplary embodiment of the present disclosure.

FIG. 4 is a block diagram schematically illustrating an art psychological analysis apparatus using voice, text, and picture data according to another exemplary embodiment of the present disclosure.

Referring to FIG. 4, in the art psychological analysis apparatus 1 according to another exemplary embodiment of the present disclosure, the emotion analysis unit 30 is divided into a first emotion analysis unit 30a and a second emotion analysis unit 30b, the first emotion analysis unit 30a is trained by the first artificial intelligence model 31a, and the second emotion analysis unit 30b may be trained by the second artificial intelligence model 31b.

The first emotion analysis unit 30a and the second emotion analysis unit 30b analyze the emotion of the user 2 from the picture data in the same way using different training techniques so that the second emotion analysis unit 30b maintains an operation standby state while the first emotion analysis unit 30a operates, but operates during the operation standby state of the first emotion analysis unit 30a to analyze the emotion of the user 2 from the picture data.

At this time, the first emotion analysis unit 30a operates when the user 2 inputs the picture subject through the user interface 10, and is switched to an operation standby state when the input of the picture subject is omitted.

As described above, as the emotion analysis unit 30 is divided into the first emotion analysis unit 30a and the second emotion analysis unit 30b, information about the psychological state of the user 2 stored in the database 60 may include information about which of the first emotion analysis unit 30a and the second emotion analysis unit 30b has analyzed the emotion of the user 2 included in the psychological state of the user 2.

In the meantime, the art psychological analysis apparatus 1 according to another exemplary embodiment of the present disclosure may further include a communication unit 70 for communication between a user 2 who is a test taker and a terminal 4 of a second user carried by a second user 3 who is a tester (a picture analysis expert).

The terminal 4 of the second user may include a second user interface which allows the user 2 to provide information about a psychological state of the user 2 analyzed by the psychological state analysis unit 50 and stored in the database 60, and to input a psychological analysis opinion about an emotion and a personality of the user 2 analyzed by the second user 3 based on the information about the psychological state of the user 2.

At this time, when it is determined that the emotion part of the user 2 is not accurately analyzed during the process of analyzing information about the psychological state of the user 2, the second user 3 may determine which one of the first emotion analysis unit 30a and the second emotion analysis unit 30b is the emotion object of the user 2, which is information included in the information about the psychological state of the user 2 to induce to accurately analyze the emotion of the user 2 by improving an error of the emotion analysis unit 30.

Further, when the psychological analysis opinion about the emotion and the personality of the user 2 is input to the terminal 4 of the second user, the database 60 stores an art psychological analysis opinion about the emotion and the personality of the user 2 analyzed by the second user 3 which is provided through the second user interface and the communication unit 70. The user interface 10 outputs the information about the psychological state of the user 2 and the art psychological analysis opinion about the emotion and the personality of the user 2 together on the display of the art psychological analysis apparatus 1, and thus may provide various art psychological analysis results to the user 2 thereby.

At this time, if the art psychological analysis opinion about the emotion and the personality of the user is stored in the database 60 while outputting the information about the psychological state of the user 2 on the display of the art psychological analysis apparatus 1, after loading (refreshing) information about the psychological state of the user 2, the user interface 10 may output the art psychological analysis opinion about the emotion and the personality of the user 2 together with the information about the psychological state of the user 2 on the display of the art psychological analysis apparatus 1.

As described above, the art psychological analysis apparatus 1 according to the exemplary embodiment of the present disclosure shares the same ground truth without causing a time difference between picture data which is directly drawn by the user 2 who is a test taker, directly input voice data, and text data extracted from the voice data to predict the psychology of the user 2 using the picture data, the voice data, and the text data.

Further, unlike the artificial intelligence model which predicts the psychology of the test taker only with the picture data, the art psychological analysis apparatus 1 uses the voice data and the text data by means of an architecture using picture data, voice data, and text data to accurately perform the direct labeling of the user 1 with the labeling at the time of the art psychological test.

As described above, the art psychological analysis apparatus 1 uses the picture data, the voice data, and the text data based on the premise of imbalance of the artificial intelligence prediction performance. The imbalance of the artificial intelligence prediction performance is caused due to the high reliance on data in the field of the artificial intelligence. The voice data and the text data which are a large amount of external data sets have a high prediction accuracy, but the picture data which has not many external datasets has a low prediction accuracy. Therefore, it has an advantage of being able to objectively predict psychology by using together with the voice data and the text data, rather than conducting the art psychological test only with the picture data.

Hereinafter, processes of an art psychological analysis method using an art psychological analysis apparatus 1 according to an exemplary embodiment of the present disclosure will be described in detail.

Figure 5:
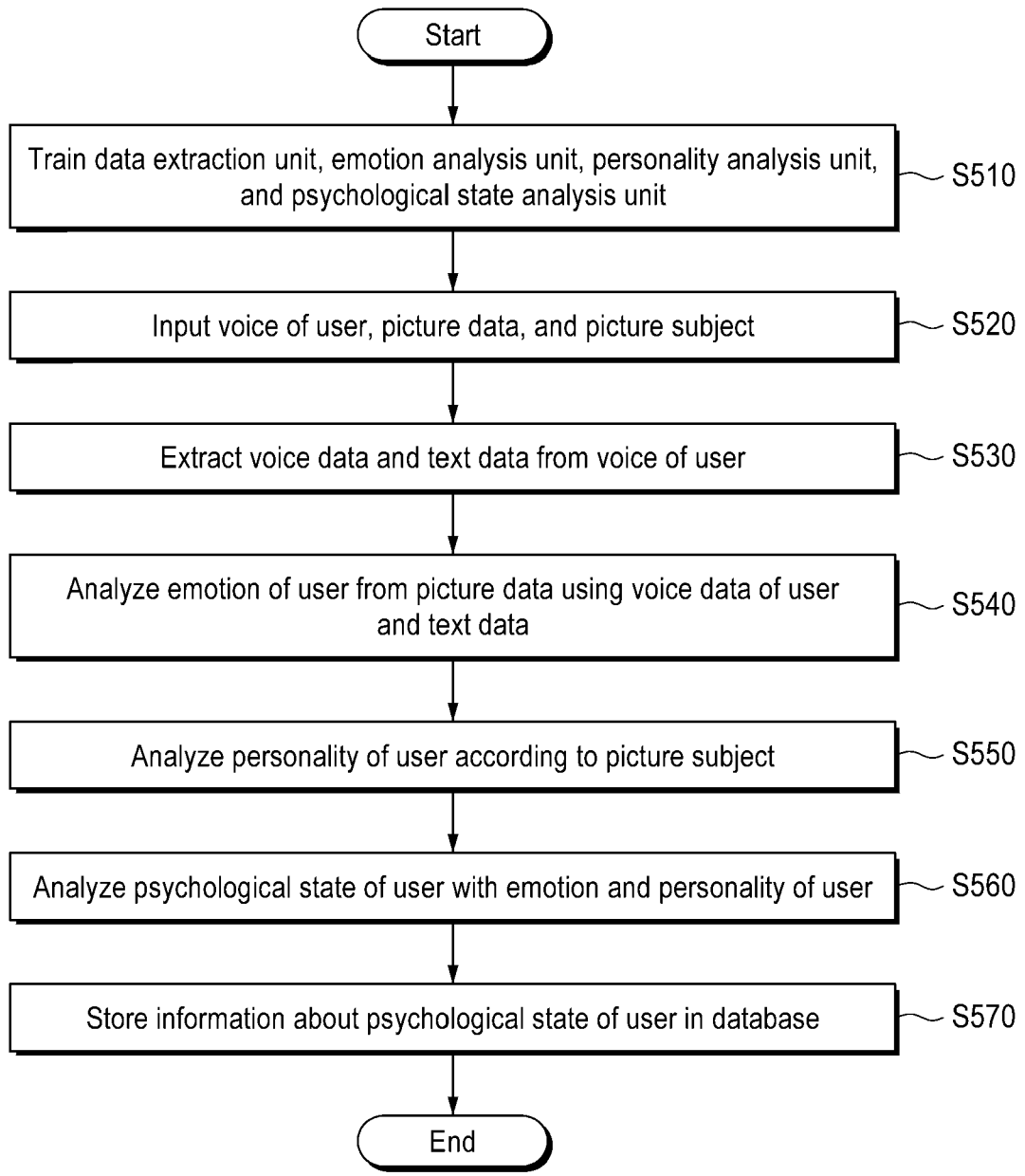
FIG. 5 is a flowchart illustrating an art psychological analysis method using an art psychological analysis apparatus using voice, text, and picture data according to an exemplary embodiment of the present disclosure.

FIG. 5 is a flowchart illustrating an art psychological analysis method using an art psychological analysis apparatus using voice, text, and picture data according to an exemplary embodiment of the present disclosure.

Referring to FIG. 5, a data extraction unit 20, an emotion analysis unit 30, a personality analysis unit 40, and a psychological state analysis unit 50 may be trained in step S510.

Next, the user 2 may input picture data, a voice, and a picture subject of the picture data to the user interface 10 during the art psychological test in step S520.

Next, the data extraction unit 20 extracts voice data from the voice of the user 2 input to the user interface 10, and may extract text data from the voice data in step S530.

Next, the emotion analysis unit 30 may analyze the emotion of the user 2 from the picture data using voice data and text data of the user 2 extracted from the data extraction unit 20 in step S540.

Next, simultaneously with the process of analyzing the emotion of the user 2 by the emotion analysis unit 30, the personality analysis unit 40 may analyze the personality of the user 2 according to a picture subject of picture data input to the user interface 10 in step S550.

Next, the psychological state analysis unit 50 may analyze the psychological state of the user 2 based on the emotion of the user 2 analyzed by the emotion analysis unit 30 and the personality of the user 2 analyzed by the personality analysis unit 40 in step S560.

Next, information about the psychological state of the user 2 analyzed by the psychological state analysis unit 50 may be stored in the database 60 in step S570.

The processes S510 to S570 of the art psychological analysis method using the art psychological analysis apparatus 1 according to the exemplary embodiment of the present disclosure may be performed by the art psychological analysis apparatus 1 which has been described with reference to FIGS. 1 to 3(*b*), and the detailed description is the same as the above-description so that a redundant description will be omitted for the sake of convenience.

Moreover, the processes of the art psychological analysis method using the art psychological analysis apparatus 1 according to the exemplary embodiment of the present disclosure may further include a process of outputting an art psychological analysis opinion about the emotion and the personality of the user 2 analyzed by the second user 3, and the processes are as follows:

Hereinafter, processes of the art psychological analysis method using the art psychological analysis apparatus 1 according to an exemplary embodiment of the present disclosure will be described in more detail with respect to the difference from the processes of the art psychological analysis method using the art psychological analysis apparatus 1 according to the exemplary embodiment of the present disclosure.

Further, the description of the processes S610 to S670 of the art psychological analysis method same as the processes of the art psychological analysis method of the exemplary embodiment in which only the reference numerals are different from those of the exemplary embodiment will be omitted for the sake of convenience.

Figure 6:
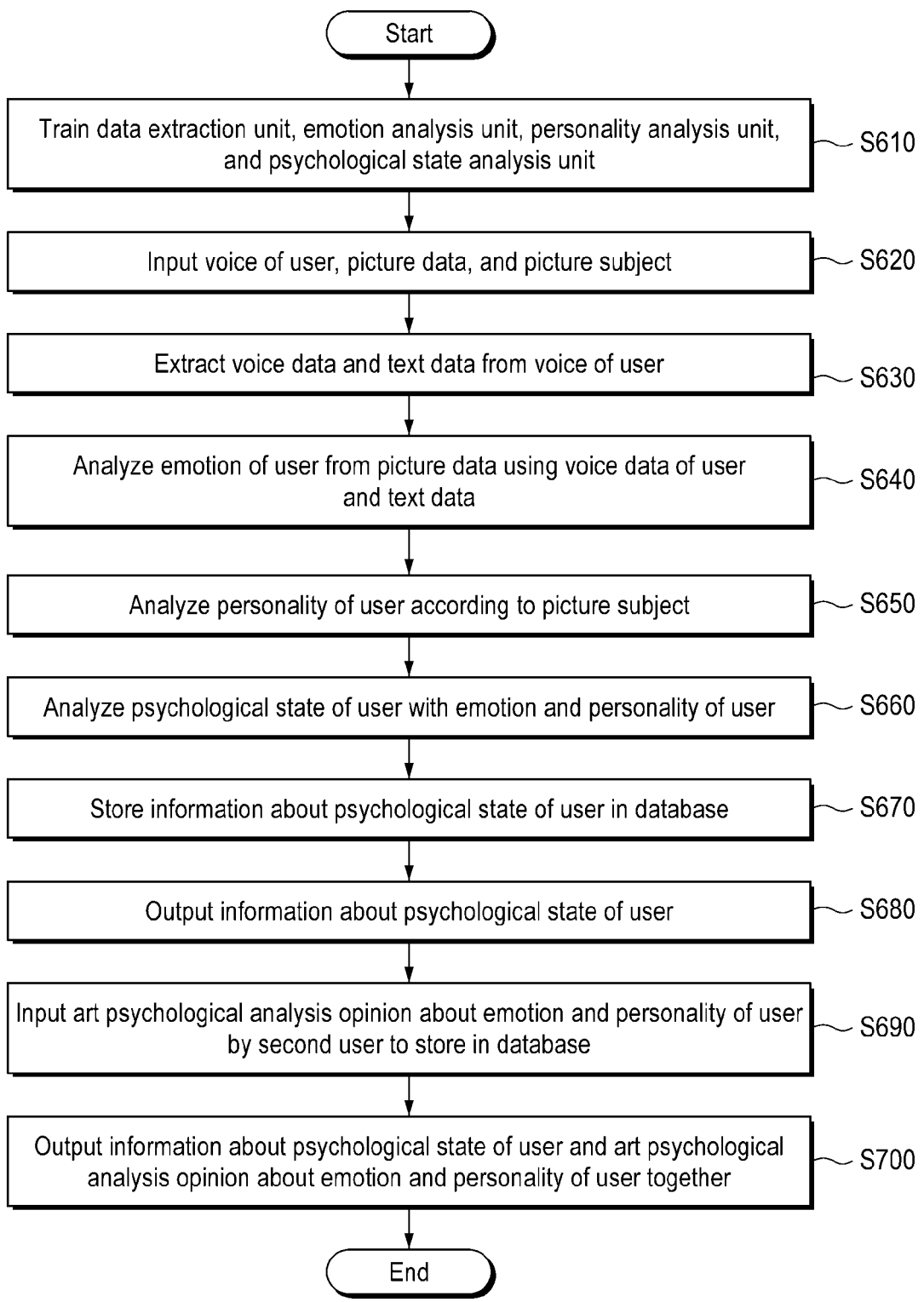
FIG. 6 is a flowchart illustrating an art psychological analysis method using an art psychological analysis apparatus using a voice, a text, and picture data according to another exemplary embodiment of the present disclosure.

FIG. 6 is a flowchart illustrating an art psychological analysis method using an art psychological analysis apparatus using voice, text, and picture data according to another exemplary embodiment of the present disclosure.

Referring to FIG. 6, information about a psychological state of the user 2 stored in the database 60 may be output onto the display of the art psychological analysis apparatus 1 through the user interface 10 in step S680.

Next, after receiving information about a psychological state of the user 2 stored in the database 60 through the second user interface and the communication unit 70 provided in the terminal 4 of the second user, the second user 3 inputs the art psychological analysis opinion about the emotion and the personality of the user 2 analyzed from the information about the psychological state of the user 2 through the second user interface and may store the art psychological analysis opinion in the database 60 in step S690.

Next, the art psychological analysis opinion about the emotion and the personality of the user 2 stored in the database 60 may be output on the display of the art psychological analysis apparatus 1 together with the information about the psychological state of the user 2 through the user interface 10 in step S700.

The processes S680 to S700 of the art psychological analysis method using the art psychological analysis apparatus 1 according to another exemplary embodiment of the present disclosure may be performed by the art psychological analysis apparatus 1 which has been described with reference to FIG. 4, and the detailed description is the same as the above-description so that a redundant description will be omitted for the sake of convenience.

In the meantime, the art psychological analysis method of the art psychological analysis apparatus 1 according to the exemplary embodiments of the present disclosure may be implemented by an application or implemented in the form of a program command which may be executed through various computer components to be recorded in a computer readable recording medium. The computer readable recording medium may include solely a program command, a data file, and a data structure or a combination thereof.

Examples of the computer readable recording medium include magnetic media such as a hard disk, a floppy disk, or a magnetic tape, optical recording media such as a CD-ROM or a DVD, magneto-optical media such as a floptical disk, and a hardware device which is specifically configured to store and execute the program command such as a ROM, a RAM, and a flash memory.

As described above, the detailed description of the exemplary embodiments of the disclosed present disclosure is provided such that those skilled in the art implement and carry out the present disclosure. While the disclosure has been described with reference to the preferred embodiments, it will be understood by those skilled in the art that various changes and modifications of the present disclosure may be made without departing from the spirit and scope of the disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the technical spirit and essential feature of the present disclosure. Therefore, the detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the embodiment or may be included as new claims by correction after application.

The invention claimed is:

1. An art psychological analysis apparatus using voice, text, and picture data, the apparatus comprising:
   a user interface for providing an interaction environment to a user who is a test taker;
   a data extraction unit which extracts voice data from a voice of the user input through the user interface during an art psychological test, and extracts text data from the voice data;
   an emotion analysis unit which analyzes an emotion of the user from picture data input by the user through the user interface using the voice data and text data extracted from the data extraction unit;
   a personality analysis unit which analyzes a personality of the user according to a picture subject of the picture data input by the user together with the picture data, through the user interface;
   a psychological state analysis unit which analyzes a psychological state of the user based on the emotion of the user analyzed by the emotion analysis unit and the personality of the user analyzed by the personality analysis unit; and
   a database which stores information about the user's psychological state analyzed by the psychological state analysis unit,
   wherein the emotion analysis unit includes an artificial intelligence model unit which performs the training using an emotion analysis model in which the training data is constructed by labeling the emotion analysis result according to the voice data and text data extracted from the voice input together with picture data through the user interface to analyze the emotion of the user,
   wherein the artificial intelligence model unit includes:
      a first artificial intelligence model which distillates by itself based on a self-distillation technique, and analyzes the emotion with picture data by smoothing the emotion analysis result of the emotion analysis model to a soft label and then by setting to a ground truth; and
      a second artificial intelligence model which is trained in advance by a pretext task set by a second user, who is a tester, based on a self-supervised learning technique, and analyzes an emotion with picture data by setting the emotion analysis result of the emotion analysis model to the ground truth as a pseudo label, and
   wherein the personality analysis unit includes a third artificial intelligence model trained to determine whether a picture subject of the picture data is valid by determining whether a distribution status of a cluster is similar to a predicted distribution status of a cluster by image clustering which divides similar picture data according to a picture subject by clusters and to classify the cluster by personalities to analyze the personality by the picture subject.

2. The art psychological analysis apparatus using voice, text, and picture data of claim 1, wherein the emotion analysis unit further includes:
   a first emotion analysis unit which is trained with the first artificial intelligence model to analyze an emotion of the user with picture data input through the user interface; and
   a second emotion analysis unit which is trained with the second artificial intelligence model to analyze an emotion of the user with picture data input through the user interface, maintains an operation standby state during the operation of the first emotion analysis unit, and operates in an operation standby state of the first emotion analysis unit.

3. The art psychological analysis apparatus using voice, text, and picture data of claim 2, wherein when the user omits the inputting of a picture subject of the picture data through the user interface, the first emotion analysis unit is switched to an operation standby state.

4. The art psychological analysis apparatus using voice, text, and picture data of claim 1, further comprising:
a communication unit which communicates with a terminal of the second user.

5. The art psychological analysis apparatus using voice, text, and picture data of claim 4, wherein the terminal of the second user includes:
a second user interface which provides, to the second user, information about a psychological state of the user analyzed by the psychological state analysis unit which is to be stored in the database, and allows the second user to input a psychological analysis opinion about an emotion and a personality of the user analyzed by the second user from information about a psychological state of the user.

6. The art psychological analysis apparatus using voice, text, and picture data of claim 5, wherein the database stores an art psychological analysis opinion about the emotion and the personality of the user which is analyzed by the second user and provided through the second user interface and the communication unit.

7. The art psychological analysis apparatus using voice, text, and picture data of claim 6, wherein when the information about the psychological state of the user is stored in the database, the user interface outputs information about the psychological state of the user, and
when an art psychological analysis opinion about the emotion and the personality of the user is stored in the database, the user interface outputs the information about the psychological state of the user along with the art psychological analysis opinion about the emotion and the personality of the user.

8. An art psychological analysis method using an art psychological analysis apparatus using voice, text, and picture data, comprising:
training a data extraction unit, an emotion analysis unit, a personality analysis unit, and a psychological state analysis unit;
inputting, by a user, picture data, voice, and a picture subject of the picture data to a user interface during an art psychological test;
extracting voice data from a voice of the user, and extracting text data from the voice data, by the data extraction unit;
analyzing an emotion of the user from the picture data using voice data and text data of the user, by the emotion analysis unit;
analyzing a personality of the user according to a picture subject of the picture data, by the personality analysis unit;
analyzing, by the psychological state analysis unit, a psychological state of the user based on an emotion of the user analyzed by the emotion analysis unit and a personality of the user analyzed by the personality analysis unit;
storing information about a psychological state of the user analyzed by the psychological state analysis unit in database;
outputting information about a psychological state of the user through the user interface;
inputting an art psychological analysis opinion about an emotion and a personality analyzed from information about a psychological state of the user by a second user interface to be stored in the database after receiving information about a psychological state of the user by a second user through the second user interface and a communication unit provided in a terminal of the second user who is a tester; and
outputting information about a psychological state of the user and an art psychological analysis opinion about an emotion and a personality of the user together through the user interface,
wherein the emotion analysis unit includes an artificial intelligence model unit which performs the training using an emotion analysis model in which the training data is constructed by labeling the emotion analysis result according to the voice data and text data extracted from the voice input together with picture data through the user interface to analyze the emotion of the user,
wherein the artificial intelligence model unit includes:
a first artificial intelligence model which distillates by itself based on a self-distillation technique, and analyzes the emotion with picture data by smoothing the emotion analysis result of the emotion analysis model to a soft label and then by setting to a ground truth; and
a second artificial intelligence model which is trained in advance by a pretext task set by the second user, who is a tester, based on a self-supervised learning technique, and analyzes an emotion with picture data by setting the emotion analysis result of the emotion analysis model to the ground truth as a pseudo label, and
wherein the personality analysis unit includes a third artificial intelligence model trained to determine whether a picture subject of the picture data is valid by determining whether a distribution status of a cluster is similar to a predicted distribution status of a cluster by image clustering which divides similar picture data according to a picture subject by clusters and to classify the cluster by personalities to analyze the personality by the picture subject.

9. A computer program stored in a computer readable recording medium to execute the art psychological analysis method using art psychological analysis apparatus using voice, text, and picture data of claim 8.

* * * * *